United States Patent
Olsson (10) Patent No.: US 11,338,055 B2
(45) Date of Patent: May 24, 2022

(54) WOUND DRESSING

(71) Applicant: Animal Ethics Pty Ltd, Yarra Glen (AU)

(72) Inventor: Charles Robert Olsson, Crestmead (AU)

(73) Assignee: Animal Ethics Pty Ltd

( * ) Notice: Subject to any disclaimer, the term of this patent is extended or adjusted under 35 U.S.C. 154(b) by 0 days.

(21) Appl. No.: 16/771,348

(22) PCT Filed: Dec. 10, 2018

(86) PCT No.: PCT/AU2018/000250
§ 371 (c)(1),
(2) Date: Jun. 10, 2020

(87) PCT Pub. No.: WO2019/113623
PCT Pub. Date: Jun. 20, 2019

(65) Prior Publication Data
US 2020/0345890 A1    Nov. 5, 2020

(30) Foreign Application Priority Data

Dec. 11, 2017    (AU) ................................ 2017904977

(51) Int. Cl.
| | | |
|---|---|---|
| *A61L 26/00* | (2006.01) |
| *A61K 9/06* | (2006.01) |
| *A61K 31/167* | (2006.01) |
| *A61K 31/136* | (2006.01) |
| *A61K 31/44* | (2006.01) |
| *A61K 47/18* | (2017.01) |
| *A61K 47/20* | (2006.01) |
| *A61K 47/38* | (2006.01) |

(52) U.S. Cl.
CPC ............ *A61L 26/0066* (2013.01); *A61K 9/06* (2013.01); *A61K 31/136* (2013.01); *A61K 31/167* (2013.01); *A61K 31/44* (2013.01); *A61K 47/18* (2013.01); *A61K 47/20* (2013.01); *A61K 47/38* (2013.01); *A61L 2300/402* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 3,365,006 A * | 1/1968 | Kupka | ...................... E02D 7/10 92/78 |
| 8,822,416 B2 | 9/2014 | Sheil et al. | |
| 8,960,128 B2 | 2/2015 | Sheil et al. | |
| 9,592,318 B2 | 3/2017 | Sheil et al. | |

FOREIGN PATENT DOCUMENTS

| | | | |
|---|---|---|---|
| CN | 101427988 A | | 5/2009 |
| CN | 102048618 | * | 5/2011 |
| CN | 102058618 A | | 5/2011 |

(Continued)

*Primary Examiner* — Melissa S Mercier
(74) *Attorney, Agent, or Firm* — The Webb Law Firm (57) ABSTRACT

This invention relates to a packaged sterile wound dressing comprising a dressing saturated with a pain relieving composition, a method of providing pain relief due to a wound of a subject using said dressing, and a method of manufacturing the packaged sterile wound dressing.

12 Claims, 3 Drawing Sheets

(56) References Cited

FOREIGN PATENT DOCUMENTS

| CN | 102266582 A | 12/2011 | | |
|---|---|---|---|---|
| CN | 105903056 A | 8/2016 | | |
| RU | 2349313 C1 | 7/2007 | | |
| WO | 2006096913 A1 | 9/2006 | | |
| WO | 2006096914 A1 | 9/2006 | | |
| WO | WO-2006096913 A1 * | 9/2006 | ............... | A61K 9/06 |
| WO | 2007143586 A2 | 12/2007 | | |
| WO | 2008151040 A2 | 12/2008 | | |
| WO | WO-2008151040 A2 * | 12/2008 | ............. | A61L 15/44 |

* cited by examiner

WOUND DRESSING

CROSS-REFERENCE TO RELATED APPLICATIONS

This application is the United States national phase of International Application No. PCT/AU2018/000250 filed Dec. 10, 2018, and claims priority to Australian Patent Application No. 2017904977, filed Dec. 11, 2017, the disclosures of which are hereby incorporated by reference in their entirety.

TECHNICAL FIELD

This invention relates to a wound dressing comprising a dressing saturated with a pain relieving composition. In a preferred embodiment, the invention concerns a sterile wound dressing comprising a dressing saturated with a pain relieving composition, contained within packaging such as a sachet.

BACKGROUND ART

Pain from a wound (eg. laceration, surgical incision, ulcer or burn) is initiated by a stimulation of traumatized nerve fibres and is intensified by a local inflammatory response that occurs over ensuing 24-48 hours and results in local tissue swelling and oedema. Pain from an open wound is also further intensified and prolonged by a sensitization reaction of higher nerve function which also occurs over ensuing hours and days, and may lead to lower pain thresholds and prolonged hypersensitivity of surrounding tissues.

Such wounds are usually treated by closing or sealing the wound, such as by suturing, adhesive plastering, bandaging or other practice. Closing the wound stops bleeding, protects traumatised tissues and nerve fibres from dehydration, ongoing environmental exposure, risk of infection and ongoing painful stimulation. Pain therefore abates as the inflammatory response and tissue oedema subsides.

In many cases, wounds cannot be treated as required and are therefore left open to heal by secondary intention. This applies to a very large number of acute traumatic and/or surgically induced wounds, particularly in animals. Examples include:
- Wounds in animals, including traumatic wounds and/or those caused by husbandry procedures such as branding and mulesing.
- Wounds assessed "in the field" by first responders in acute human trauma situations, such as accidents or fires, or mass human trauma situations, such as earthquakes, floods and wars.
- Wounds that occur in remote locations and Third World countries where medical attention may be limited or unavailable.

The inventor's earlier patents U.S. Pat. Nos. 8,822,416, 8,960,128 and 9,592,318 describe topical analgesic and anaesthetic compositions, which in one commercial form is marketed under the trade mark Tri-solfen™. Although the commercial form is used for wound and pain management in livestock, it also has applications for human use. The commercial form was found to provide extended analgesia and promote wound healing. The current commercial form is a spray-on anaesthetic gel, applied by way of a spray applicator. The current commercial form can also be dripped onto a wound. Once sprayed or dripped onto a wound, the anaesthetic gel becomes very sticky and seals the wound. The current commercial form is a liquid and is dispensed from a container.

It is not always practical, possible, convenient or cost-effective to transport a liquid to a place where medical attention is required, particularly if the place is in a remote location. Also, it is not always practical, possible or convenient to spray or drip a pain relieving composition onto a wound.

DISCLOSURE OF INVENTION

An object of the present invention is to provide a pain relieving wound dressing that overcomes or minimises a disadvantage mentioned above.

Alternatively, it is an object of the present invention to provide the consumer with a useful commercial choice.

According to a $1^{st}$ aspect of the present invention, there is provided a wound dressing comprising a dressing saturated with a pain relieving composition.

According to a $2^{nd}$ aspect of the present invention, there is provided a sterile wound dressing comprising a dressing saturated with a pain relieving composition contained within packaging.

According to a $3^{rd}$ aspect of the present invention, there is provided a method of providing pain relief due to a wound of a subject, said method comprising the step of applying a wound dressing according to the $1^{st}$ or $2^{nd}$ aspect of the present invention to a wound of a subject.

According to a $4^{th}$ aspect of the present invention, there is provided a method of manufacturing a sterile wound dressing according to the $1^{st}$ or $2^{nd}$ aspect of the present invention, said method comprising the step of packaging a dressing saturated with a pain relieving composition in a sterile manner so as to produce a sterile wound dressing.

According to a $5^{th}$ aspect of the present invention, there is provided use of the wound dressing of the $1^{st}$ aspect in the preparation of a medicament for providing pain relief due to a wound of a subject.

The term "wound" is to be understood as including: a minor cut, scratch, sting, burn and abrasion; and, a laceration, surgical incision, ulcer, major abrasion and major burn.

The dressing is designed to be in direct contact with the wound, as distinguished from a bandage, which is most often used to hold a dressing in place.

In some embodiments, the wound dressing comprises a dressing saturated (or supersaturated) with a pain relieving composition. As used herein the term "dressing" is to be understood as being applied to a wound or to clean the wound, in which latter case it may be called a wipe, gauze or towelette.

The dressing can be of any suitable size, shape and construction and can be made of any suitable material or materials. For example, it can comprise a woven material, non-woven material, a combination of woven materials, a combination of non-woven materials, a combination of woven and non-woven materials, an open weave fabric, fabric, gauze, cloth or plastic film. It can be made of cotton. It can be made from substances impervious to moisture, such as plastic or latex, so as to increase the rate of absorption of the pain relieving composition into the wound. It can be made from a polymer such as polyester.

Preferably the dressing has an open pore structure or is open weave. Preferably the dressing does not stick to the wound. The dressing can be impregnated with petroleum jelly (eg. Vasoline™) or other non-stick substance. Preferably fibres of the dressing do not stick to the wound.

Preferably the dressing can be supersaturated with the pain relieving composition and released to the wound.

The dressing can be of any suitable width and length. For example, it can be anywhere between 50 and 200 millimetres wide and 50 and 300 mm long (including all ~5 mm increments from 50 to 300). In some embodiments, the dressing is about 150 mm×220 mm.

In some embodiments the dressing can be made of cotton, such as woven cotton. In some embodiments the dressing can be a plastic or polymer gauze. In some embodiments the dressing can be made of polyester or other type of polymer. Preferably the dressing is made from 100% polyester.

In some embodiments, the saturated dressing has one or more of the following properties, but preferably all of the following properties:
  It stems bleeding.
  It helps seal the wound.
  It protects the wound from infection (both against germs and mechanical damage).
  It eases pain
  It prevents further trauma to the wound.
  It debrides the wound.
  It obscures the wound from view, and therefore lessen psychological stress.

Preferably, the saturated dressing both eases wound pain and reduces the risk of infection. Preferably the saturated dressing promotes healing of the wound. Preferably the saturated dressing promotes granulation and epithelialisation of the wound.

In some embodiments the dressing can be secured over the wound with adhesive tape and/or a bandage. For example, the wound dressing can comprise an adhesive backing or plaster backing for holding the dressing over a wound. For example, the wound dressing can be in the form of an adhesive patch or strip.

Any suitable type of pain relieving composition can be used. The composition can be, for example, in the form of a liquid, ointment, gel, lotion, cream, creme, emulsion, paste, film or suspension. In some embodiments the pain relieving composition is in the form of a liquid that sets as a sticky viscous gel when exposed to the wound.

Depending on the form of the composition, the composition can include one or more of the following types of ingredients: aqueous or oily diluent, excipient or base; buffer; bittering agent (i.e. foul-tasting agent); suspending agent; emulsifier; emollient; humectant; stabilising agent; dispersing agent; solubiliser; skin conditioning agent; skin protectant; skin penetration enhancer; fragrance; preservative; propellant; sunscreen agent; surfactant; textural modifier; colourant; and, waterproofing agent.

Suitable oily or aqueous bases, carriers, diluents and excipients are inert and physiologically acceptable and include, for example: bacteriostatic saline (saline containing benzyl alcohol), cetomacrogol, cetyl alcohol, glycerine, lanolin, petrolatum based creams, gels, hydrogels, saline, short chain alcohols and glycols (e.g. ethyl alcohol and propylene glycol), and water.

Suitable adhesives, thickening agents, gelling agents and/or viscosity increasing agents include: acrylamides copolymer, agarose, amylopectin, calcium alginate, calcium carboxymethyl cellulose, carbomer, carboxymethyl chitin, castor oil derivatives, cellulose gum, cellulosic preparation, cetyl alcohol, cetostearyl alcohol, dextrin, gelatin, hydroxy cellulose, hydroxyethylcellulose, hydroxypropylcellulose, hydroxypropyl starch, inert sugar, magnesium alginate, methyl cellulose, microcrystalline cellulose, pectin, PEG's, polyacrylic acid, polymethacrylic acid, polyvinyl alcohol, quaternium ammonium compound of bentonite or zinc stearate, sorbitol, PPG's, sodium acrylates copolymer, sodium carrageenan, xanthum gum, and yeast beta-glucan.

Either water in oil or oil in water emulsions can be used. Examples of suitable surfactants and emulsifying agents include: non-ionic ethoxylated and non-ethoxylated surfactants, abietic acid, almond oil PEG, beeswax, butylglucoside caprate, $C_{18}$-$C_{36}$ acid glycol ester, $C_9$-$C_{15}$ alkyl phosphate, caprylic/capric triglyceride PEG-4 esters, cetomacrogol, ceteareth-7, cetereth-20, cetyl phosphate, cetyl stearyl alcohol, corn oil PEG esters, DEA-cetyl phosphate, dextrin laurate, dilaureth-7 citrate, dimyristyl phosphate, glycereth-17 cocoate, glyceryl erucate, glycerol, glyceryl laurate, G.M.S. acid stable, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPGs, raffinose myristate, sodium caproyl lactylate, sodium caprylate, sodium cocoate, sodium isostearate, sodium tocopheryl phosphate, steareths, TEA-$C_{12}$-$C_{13}$ pareth-3 sulfate, tri-$C_{12}$-$C_{15}$ pareth-6 phosphate, and trideceths.

The composition can include one or more types of preservative. A suitable preservative, for example, can be: benzalkonium chloride, benzoic acid, benzothonium chloride, benzyl alcohol, 2-bromo-2-nitropropane-1,3-diol, bronopol, butylated hydroxyanisole, butylated hydroxytoluene, butyl paraben, chlorophene, chlorphenesin, diazolidinyl urea, DMDM hydantoin, ethyl paraben, formaldehyde-releasing preservative, hydroquinone, iodopropynyl butyl carbamate, imidazolidinyl urea, methyldibromo glutaronitrile, methylhydroquinone, methylisothiazolinone, methyl paraben, nitrosamines, o-cymen-5-ol, phenoxyethanol, propyl paraben, quaternium-15, sodium benzoate, sodium dehydroacetate, sodium hydroxymethylglycinate, sodium metabisulfite, and sodium sulfite.

Preferably, the composition includes the reducing agent sodium metabisulfite so as to enhance the stability of the vasoconstrictor.

A skin conditioning agent, as defined herein, improves dry or damaged skin. Such agents, for example, include: acetyl cysteine, N-acetyl dihydrosphingosine, acrylates/behenyl acrylate/dimethicone acrylate copolymer, adenosine, adenosine cyclic phosphate, adensosine phosphate, adenosine triphosphate, alanine, albumen, algae extract, allantoin and deriviatives, aloe barbadensis extracts, aluminum PCA, amyloglucosidase, arbutin, arginine, azulene, bromelain, buttermilk powder, butylene glycol, caffeine, calcium gluconate, capsaicin, carbocysteine, carnosine, beta-carotene, casein, catalase, cephalins, ceramides, chamomilla recutita (matricaria) flower extract, cholecalciferol, cholesteryl esters, coco-betaine, coenzyme A, corn starch modified, crystallins, cycloethoxymethicone, cysteine DNA, cytochrome C, darutoside, dextran sulfate, dimethicone copolyols, dimethylsilanol hyaluronate, DNA, elastin, elastin amino acids, epidermal growth factor, ergocalciferol, ergosterol, ethylhexyl PCA, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, kinetin, lactoferrin, lanosterol, lauryl PCA, lecithin, linoleic acid, linolenic acid, lipase, lysine, lysozyme, malt extract, maltodextrin, melanin, methionine, mineral salts, niacin, niacinamide, oat amino acids, oryzanol, palmitoyl hydrolyzed proteins, pancreatin, papain, PEG, pepsin, phospholipids, phytosterols, placental enzymes, placental lipids, pyridoxal 5-phosphate, quercetin, resorcinol acetate, riboflavin, RNA, saccharomyces lysate extract, silk amino acids, sorbitol, sphingolipids, stearamidopropyl betaine, stearyl palmitate, tocopherol, tocopheryl acetate, tocopheryl linoleate, ubiquinone, *Vitis vinifera* (grape) seed oil, wheat amino acids, xanthan gum, and zinc gluconate.

The composition can include a skin penetration enhancer for enhancing the penetration of active ingredients, such as an anaesthetic agent. Any suitable type of enhancer can be used. Examples of suitable enhancers may include solvents, detergents or low carbon alcohols such as dimethylsulfoxide, oleyl alcohol, propylene glycol, methyl pyrrolidone and dodecylazyl cycloheptan 2-one.

The composition can comprise a hydrophilic or hydroalcoholic gelling agent. Preferably, the composition comprises about 1 to 20 g per litre of at least one type of gum or cellulosic preparation (as well as all 0.1 g increments between 1 and 20). More preferably, the composition comprises a polyhydric alcohol in combination with a cellulosic preparation. Even more preferably, the composition comprises about 5 mg/mL hydroxy cellulose in combination with about 100 mg/mL non-crystallising liquid sorbitol (70%).

The composition is preferably capable of also promoting and prolonging contact of other active agents of the composition with the wound.

The pain relieving composition can comprise any suitable type of pain relieving agent or agents. The pain relieving agent can be an anaesthetic agent or an analgesic agent, such as an anti-inflammatory agent. In some embodiments, at least one anaesthetic agent is used. In some embodiments at least one analgesic agent is used. In some embodiments, at least one analgesic agent is used in combination with at least one anaesthetic agent. Examples of anaesthetic agents include: lignocaine, chloroprocaine, mepivacaine, bupivacaine, articaine, etidocaine, levobupivacaine, tetracaine, prilocaine, benzocaine, ropivacaine, cocaine, oxyprocaine, hexylcaine, dibucaine, piperocaine and procaine and pharmaceutically acceptable acids, bases and salts thereof.

Examples of other potentially suitable anaesthetic agents include: butamben, butambenpicrate, dimethisoquin hydrochloride, diperodon, diphenhydramine, dyclonine, ketamine, methapyriline, p-buthylaminobenzoic acid, 2-(die-ethyl amino) ethyl ester hydrochloride, pramoxine and tripelennamine.

The composition preferably provides maximum anaesthesia with minimal risk of toxicity. The formulation of the composition can be varied, as required, for potency, speed of onset and duration of anaesthetic action.

In some embodiments, the composition comprises at least one local anaesthetic agent. In some embodiments, the composition comprises at least one local anaesthetic agent having a rapid onset of action. In some embodiments, the composition comprises at least one local anaesthetic agent having a long duration of action. In some embodiments, the composition comprises both at least one local anaesthetic agent having a rapid onset of action and at least one local anaesthetic agent having a long duration of action. It is to be understood that some local anaesthetic agents can provide both a rapid onset of action and long duration of action, such as amethocaine, so the local anaesthetic agent providing a rapid onset of action and local anaesthetic agent providing a long duration of action can be one and the same.

Anaesthetic agents that usually have a rapid onset of action (usually between about 5-10 minutes) include lignocaine, prilocaine, amethocaine/tetracaine and cocaine.

Anaesthetic agents that usually have a much slower onset of action but a much greater duration of action (usually between about 4-12 hours of anaesthesia) include bupivacaine, ropivacaine, levo-bupivacaine, and amethocaine/tetracaine. Bupivacaine may typically provide up to about 6-12 hours of anaesthesia, depending on the method of administration.

Any suitable amount of anaesthetic agent can be used in the composition but preferably about 0.01-10 weight/volume % of anaesthetic agent is used (as well as all 0.01 increments between 0.01 and 10, eg. 0.01, 0.02 etc).

Any suitable amount of rapid onset anaesthetic agent can be used in the composition but preferably about 0.01-10 weight/volume % of anaesthetic agent is used (as well as all 0.01 increments between 0.01 and 10). Preferably, about 2-8 weight/volume % anaesthetic agent is used in those situations where a rapid onset of action is required (as well as all 0.01 increments between 2 and 8). More preferably, about 5% weight/volume anaesthetic agent is used.

In some embodiments, about 1-10 weight/volume % lignocaine is used (as well as all 0.01 increments between 1 and 10, eg. 0.01, 0.02 etc). In some embodiments, about 2-8 weight/volume % lignocaine is used as the anaesthetic agent in those situations where a rapid onset of action is required (as well as all 0.01 increments between 2 and 8). In some embodiments, about 5% lignocaine is used.

Any suitable amount of long duration of action anaesthetic agent can be used in the composition but preferably about 0.01-10 weight/volume % of anaesthetic agent is used (as well as all 0.01 increments between 0.01 and 10). Preferably, about 0.1-5 weight/volume % anaesthetic agent is used in those situations where a long duration of action is required (as well as all 0.01 increments between 0.1 and 5). More preferably, about 0.5% weight/volume anaesthetic agent is used.

In some embodiments, the composition can comprise any suitable amount of bupivacaine if lignocaine or other rapid onset anaesthetic agent has an inadequate duration of action. Preferably, the composition comprises about 0.1-5 weight/volume % bupivacaine (as well as all 0.01 increments between 0.1 and 5), and more preferably about 0.5% bupivacaine.

In some embodiments, the composition can comprise any suitable amount of tetracaine. Preferably, the composition comprises about 1-10 weight/volume % tetracaine (as well as all 0.01 increments between 1 and 10).

In some embodiments, at least one analgesic agent and/or at least one anti-inflammatory agent can be used. Examples of potentially suitable analgesic and/or anti-inflammatory agents include: 1-menthol, acetaminophen, alclofenac, aspirin, bendazac, betamethasone, bufexemacpiroxicam, camphor, choline salicylate, clidanac, clofezone, corticosterone, cortisone, dexamethasone, diclofenac, diflunisal, fenbufen, fenoprofen, fentiazac, fludrocortisone, fluocinolone, fluphenamic acid, flurandrenolide, flurbiprofen, glycol salicylate, halcinonide, hydrocortisone, ibuprofen, indomethacin, indoprofen, ketoprofen, meclofenamate sodium, mefenamic acid, medrysone, mepirizole, methylprednisolone, methyl salicylate, naproxene, oxyphenbutazone, paramethasone, pentazocine, phenylbutazone, piroxicam, prednisone, prednisolone, protizidic acid, pranoprofen, salicylic acid, sulindac, suprofen, tiaprofenic acid, tolmetin and triamcinolone.

Potentially suitable analgesic agents include one or more of the following: acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, pranoprofen, fenoprofen, sulindac, fenbufen, clidanac, flurbiprofen, indoprofen, protizidic acid, fentiazac, tolmetin, tiaprofenic acid, bendazac, bufexemacpiroxicam, phenylbutazone, oxyphenbutazone, clofezone, pentazocine, mepirizole, hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, naproxen, suprofen, piroxicam, diflunisal, meclofenamate sodium, carprofen, flunixin, tolfenamic acid and meloxicam.

Potentially suitable non-steroidal anti-inflammatory drug (NSAIDs) include one or more of the following: salicylate (e.g. aspirin (acetylsalicylic acid), diflunisal (dolobid), salicylic acid and other salicylates, salsalate (disalcid)), propionic acid derivative (e.g. ibuprofen, dexibuprofen, naproxen, fenoprofen, ketoprofen, dexketoprofen, flurbiprofen, oxaprozin, loxoprofen), acetic acid derivative (e.g. indomethacin, tolmetin, sulindac, etodolac, ketorolac, diclofenac, aceclofenac, nabumetone), enolic acid (oxicam) derivative (e.g. piroxicam, meloxicam, tenoxicam, droxicam, lornoxicam. isoxicam, phenylbutazone), anthranilic acid derivative (fenamate) (e.g. mefenamic acid, meclofenamic acid, flufenamic acid, tolfenamic acid), selective COX-2 inhibitor (e.g. celecoxib, rofecoxib, valdecoxib, parecoxib, lumiracoxib, etoricoxib, firocoxib), sulfonanilide (e.g. nimesulide), or other (e.g. clonixin, licofelone, H-harpagide in Figwort or Devil's Claw).

In some embodiments approximately 0.1% (1 mg/ml) meloxicam or other NSAID is used.

Any suitable amount of analgesic or anti-inflammatory agent can be used in the composition but preferably about 0.01-10 weight/volume % of agent is used (as well as all 0.01 increments between 0.01 and 10).

The composition can further include a vasoconstrictor to decrease the rate of vascular absorption of the pain relieving agent, so to improve the depth and duration of pain relieving agent, to reduce bleeding from a wound of the subject, as well as to reduce systemic toxicity. Any suitable type of vasoconstrictor can be used, including any suitable salt or form thereof. Suitable vasoconstrictors include, for instance, adrenaline (epinephrine), noradrenalin (norepinephrine) and fenylpressin, including any suitable salt or form thereof. Preferably, the composition includes about 1:1000-1:10,000 vasoconstrictor (as well as all 10 factor increments between 1000 to 10,000), and more preferably 1:2,000 vasoconstrictor. Preferably the vasoconstrictor is adrenaline.

The composition can include one or more other active ingredients. An active ingredient, as defined herein, is a compound that provides benefit to the subject. The active ingredient can be, for instance, an antibody, anticoagulant, antiproliferative, cytokine, cytotoxin, growth factor, interferon, haemostatic agent, hormone, lipid, demineralized bone or bone morphogenetic protein, cartilage inducing factor, oligonucleotide, polymer, polysaccharide, polypeptide, protease inhibitor, vitamin, mineral, antiseptic agent, insecticide or insect repellent, antibiotic or antifungal agent.

The composition preferably includes an antiseptic agent to, amongst other things, minimize wound contamination and infection. Any suitable type of antiseptic agent can be used. Suitable antiseptic agents include cetrimide, povidone-iodine, chlorhexidine, iodine, benzalkonium chloride, benzoic acid, nitrofurazone, benzoyl peroxide, hydrogen peroxide, hexachlorophene, phenol, resorcinol and cetylpyridinium chloride.

The composition can include an insecticide or insect repellent to stop insects from infesting a wound of the subject. Any suitable type of insecticide or insect repellent can be used. Examples of suitable insecticides include: trichlorfon, triflumeron, fenthion, bendiocarb, cyromazine, dislubenzuron, dicyclanil, fluazuron, amitraz, deltamethrin, cypermethrin, chlorfenbinphos, flumethrin, ivermectin, abermectin, avermectin, doramectin, moxidectin, zeti-cypermethrin, diazinon, spinosad, imidacloprid, nitenpyran, pyriproxysen, sipronil, cythioate, lufenuron, selamectin, milbemycin oxime, chlorpyrifos, coumaphos, propetamphos, alpha-cypermethrin, high cis cypermethrin, ivermectin, diflubenzuron, cyclodiene, carbamate and benzoyl urea.

The composition can comprise a colouring agent/colourant such that application of the composition to the wound can be easily assessed by eye. The colourant can be a pigment and/or dye. Suitable colourants include, for example, common food dyes or the ORCODERM®, ORCOBRITE® and ORCOFUR® lines of pigments and dyes sold by the Organic Dyestuffs Corporation. Preferably, the colourant is non-toxic and will not permanently stain the skin or animal hide.

The subject can be a human. The subject can be a mammal. The subject can be an animal such as a sheep, horse, cow, goat, pig, dog or cat. The subject can be another type of animal.

The wound dressing can be used to cover large wounds/large surface areas, such as large burns or abrasions. The dressing can be extended around a limb to cover a large surface area of the limb. The dressing can be used in conjunction with other like dressings to cover large surface areas.

The wound dressing can be used for an animal husbandry procedure. The procedure can be, for example, mulesing, shearing, ear tagging, branding, marking, or treating an open wound, eg. caused by accident or surgery.

In a first preferred embodiment, the pain relieving composition comprises:
 about 100 mg/mL non-crystallising liquid sorbitol (70%);
 about 50.0 mg/mL lignocaine HCl;
 about 5.0 mg/mL bupivacaine HCl;
 about 1.5 mg/mL sodium metabisulfite;
 about 5.0 mg/mL cetrimide;
 about 45.0 µg/mL adrenaline tartrate;
 about 5.0 mg/mL hydroxy cellulose; and optionally
 dye.

If desired, lignocaine can be swapped out and tetracaine swapped in at about 1-10%, but preferably about 5% (50 mg/mL).

In a second preferred embodiment, the pain relieving composition comprises:
 about 100 mg/mL non-crystallising liquid sorbitol (70%);
 about 40.0 mg/mL lignocaine HCl;
 about 1.5 mg/mL sodium metabisulfite;
 about 5.0 mg/mL cetrimide;
 about 36.0 µg/mL adrenaline tartrate;
 about 5.0 mg/mL hydroxy cellulose; and optionally
 dye.

If desired, lignocaine can be swapped out and tetracaine swapped in at about 1-10%, but preferably about 5% (50 mg/mL).

In a third preferred embodiment, the pain relieving composition comprises:
 about 100.0 mg/mL purified water sorbitol liquid 70% non-crystallising;
 about 50.0 mg/mL (5%) tetracaine HCl;
 about 1.5 mg/mL sodium metabisulfite;
 about 5.0 mg/mL cetrimide;
 about 45.0 µg/mL adrenaline tartrate;
 about 5.0 mg/mL hydroxy cellulose;
 to 1 mL purified water; and optionally food dye (quantity to suit (q.s.)).

In a fourth preferred embodiment, the pain relieving composition comprises: lignocaine, bupivacaine, adrenaline, cetrimide, 2-ethyl hydroxycellulose, sodium metabisulfite, liquid sorbitol (70%), buffer, and, optionally dye.

If desired, lignocaine can be swapped out and tetracaine swapped in at about 1-10%, but preferably about 5% (50 mg/mL).

In a fifth preferred embodiment, the pain relieving composition comprises: amethocaine/tetracaine, adrenaline, cetrimide, 2-ethyl hydroxycellulose, sodium metabisulfite, liquid sorbitol (70%), buffer, and, optionally, dye.

Any suitable type of packaging can be used. For example, the packaging can be in the form of a sealed wrapper, bag or sachet. The packaging can be of any suitable size and volume. Typically the packaging size and volume will be determined by the size of the dressing. The dressing will typically be folded to fit within smaller packaging.

Preferably the packaging has low linting properties.

In some embodiments the packaging is in the form of a sachet. In some embodiments, the sachet is made from a six layer mixture of polyester, polyethylene and aluminium. The sachet can be a tear-open sachet.

Any suitable volume of the pain relieving composition can be added to the packaging or contained by the packaging. Ultimately the quantity will depend on the size of the dressing. The volume can range between about 1 to 20 ml (including all 0.1 ml increments between 1 and 20). In preferred embodiments 4-10 ml and more preferably 6-8 ml and even more preferably about 7 ml of the pain relieving composition is added to the packaging or contained within the packaging.

The sterile wound dressing can be manufactured in any suitable way. Manufacture will depend on the nature of the packaging, dressing and composition.

In some embodiments a dry dressing is added to a sachet. Typically the dry dressing will be folded into a compact form.

In some embodiments a dry 100% polyester dressing/wipe is inserted into a sachet. In some embodiments the dressing/sachet combination is sterilised, preferably by gamma irradiation. A dry folded dressing/wipe in an open sachet can be Gamma irradiated at a minimum of 25 kgy and a maximum of 45 kgy.

The dressing/sachet combination can be fed into a filling machine. The filling machine can be an adapted form of a fill and seal machine that is generally used for the manufacture of an individual towelette in a sachet.

Ingredients of the pain relieving composition can be blended together and sterilised. Any suitable sterilisation step can be used to sterilise the composition. For example, the composition can be passed through one or more 0.2 micron filters before being fed to a filling machine.

The filling machine can fill the sachet with a suitable volume of the pain relieving composition to saturate the dressing, and then seal the sachet. The sachet can be heat sealed.

Having broadly described the invention in its various embodiments, non-limiting examples of embodiments will now be given.

DESCRIPTION OF PREFERRED EMBODIMENTS

Example 1—Formulation of a Pain Relieving Composition for Wounds Having a Long Duration of Action This Example describes the preparation of a particularly preferred topical analgesic pain relieving composition. The composition is in the form of a gel that provides a prolonged analgesic effect. The composition has the following formulation:

| | |
|---|---|
| Purified water Sorbitol Liquid 70% Non-Crystallising | 100.0 mg/mL |
| Lignocaine HCl | 50.0 mg/mL (5%) |
| Bupivacaine HCl | 5.0 mg/mL (0.5%) |
| Sodium Metabisulfite | 1.5 mg/mL |
| Cetrimide | 5.0 mg/mL |
| Adrenaline Tartrate | 45.0 µg/mL |
| Hydroxy Cellulose | 5.0 mg/mL |
| Purified water | to 1 mL |
| Optional: | |
| Food Dye (e.g. brilliant blue) | Quantity to suit (q.s.) |

The composition is prepared by combining/blending the above ingredients to achieve the required consistency.

If desired, the composition can further comprise an anti-inflammatory agent (e.g. isoflupredone acetate or meloxicam 0.1%, 1 mg/ml), and/or an insecticide/insect repellent such as diazinon, spinosad or cyromazine (at about 1 mg/mL), and/or a skin penetrating enhancer, and/or a bittering agent.

If desired, lignocaine can be swapped out and tetracaine swapped in at about 1-10%, but preferably about 5% (50 mg/mL).

Example 2—Formulation of a Pain Relieving Composition for Wounds

This Example describes the preparation of another preferred pain relieving composition. The composition is in most respects the same as the composition of Example 1, except that it excludes bupivacaine. The composition has the following formulation:

| | |
|---|---|
| Purified water Sorbitol Liquid 70% Non-Crystallising | 100.0 mg/mL |
| Lignocaine HCl | 40.0 mg/mL (4%) |
| Sodium Metabisulfite | 1.5 mg/mL |
| Cetrimide | 5.0 mg/mL |
| Adrenaline Tartrate | 36.0 µg/mL (1:2000) |
| Hydroxy Cellulose | q.s. |
| Purified water | to 1 mL |
| Optionally: | |
| Food Dye (e.g. blue) | q.s. |

The composition is prepared by combining/blending the above ingredients to achieve the required consistency.

If desired, the composition can further comprise an insecticide/insect repellent such as cyromazine or spinosad (at about 1 mg/mL), an NSAID (e.g. meloxicam 0.1%, 1 mg/ml), and/or a skin penetrating enhancer.

If desired, lignocaine can be swapped out and tetracaine swapped in at about 1-10%, but preferably about 5% (50 mg/mL).

Example 3—Formulation of a Topical Anaesthetic Creme Having a Long Duration of Action This Example describes the preparation of another topical pain relieving composition in the form of a creme. The composition has the following formulation:

| | |
|---|---|
| Cetyl Alcohol | 78.00 mg/mL |
| Paraffin Wax | 135.00 mg/mL |
| Glycerol | 75.00 mg/mL |
| Lauryl Sulfate | 10.00 mg/mL |
| Lignocaine HCl | 50.00 mg/mL |
| Bupivacaine HCl | 5.00 mg/mL |
| Sodium Metabisulfite | 1.50 mg/mL |
| Cetrimide | 5.00 mg/mL |
| Hydrochloric Acid 25% | q.s. |
| Adrenaline Acid Tartare | 0.045 mg/mL |
| Purified Water | to 1 mL |

The composition is prepared by combining the above ingredients to achieve the required consistency as required. The composition is in the form of a "sticky" creme.

If desired, the composition can further comprise an anti-inflammatory agent (e.g. meloxicam 0.1%, 1 mg/ml), and/or an insecticide/insect repellent, and/or a skin penetrating enhancer, and/or a bittering agent.

If desired, lignocaine can be swapped out and tetracaine swapped in at about 1-10%, but preferably about 5% (50 mg/mL).

Example 4—Formulation of a Topical Anaesthetic Gel Having a Long Duration of Action This example describes the preparation of another topical anaesthetic composition having a gum base. The composition has the following formulation:

| | |
|---|---|
| Xanthum Gum | 10.00 mg/mL |
| Gum Arabic | 1.00 mg/mL |
| Sorbitol Liquid | 100.00 mg/mL |
| Lignocaine HCl | 50.00 mg/mL |
| Bupivacaine HCl | 5.00 mg/mL |
| Sodium Metabisulfite | 1.50 mg/mL |
| Cetrimide | 5.00 mg/mL |
| Hydrochloric Acid 25% | q.s. |
| Adrenaline Acid Tartare | 0.045 mg/mL |
| Purified Water | to 1 mL |
| Optional: | |
| Dye | q.s. |

The composition is prepared by combining the above ingredients to achieve the required consistency. The composition is in the form of a "sticky" gel.

If desired, the composition can further comprise an anti-inflammatory agent (e.g. meloxicam 0.1%, 1 mg/ml), and/or an insecticide/insect repellent, and/or a skin penetrating enhancer, and/or a bittering agent.

If desired, lignocaine can be swapped out and tetracaine swapped in at about 1-10%, but preferably about 5% (50 mg/mL).

Example 5—Formulation of a Topical Anaesthetic Gel Having a Long Duration of Action This Example describes the preparation of another topical anaesthetic composition having a polyacrylic acid base. The composition has the following formulation:

| | |
|---|---|
| Polyacrylic Acid | 10.00 mg/mL |
| Sodium Hydroxide | q.s. |
| Polyhydrogenated Castor Oil | 10.00 mg/mL |
| Sorbitol Liquid | 100.00 mg/mL |
| Lignocaine HCl | 50.00 mg/mL |
| Bupivacaine HCl | 5.00 mg/mL |
| Sodium Metabisulfite | 1.50 mg/mL |
| Cetrimide | 5.00 mg/mL |
| Hydrochloric Acid 25% | q.s. |
| Adrenaline Acid Tartare | 0.045 mg/mL |
| Purified Water | to 1 mL |
| Optional: | |
| Dye | q.s. |

The composition is prepared by combining the above ingredients to achieve the required consistency. The composition is in the form of a "sticky" gel.

If desired, the composition can further comprise an anti-inflammatory agent (e.g. meloxicam 0.1%, 1 mg/ml), and/or an insecticide/insect repellent, and/or a skin penetrating enhancer, and/or a bittering agent.

If desired, lignocaine can be swapped out and tetracaine swapped in at about 1-10%, but preferably about 5% (50 mg/mL).

Example 6—Formulation of a Topical Anaesthetic Gel Having an Insecticide and a Skin Penetrating Enhancer This Example describes the preparation of another topical anaesthetic composition in the form of a spray-on gel having an insecticide (spinosad) as well as a skin penetrating enhancer (propylene glycol). The composition has the following formulation:

| | |
|---|---|
| Cellulose | 5.00 mg/mL |
| Spinosad | 1.25 mg/mL |
| Propylene Glycol | 100.00 mg/mL |
| Sorbitol Liquid | 50.00 mg/mL |
| Lignocaine HCl | 50.00 mg/mL |
| Bupivacaine HCl | 5.00 mg/mL |
| Sodium Metabisulfite | 1.50 mg/mL |
| Cetrimide | 5.00 mg/mL |
| Hydrochloric Acid 25% | q.s. |
| Adrenaline Acid Tartare | 0.045 mg/mL |
| Purified Water | to 1 mL |
| Optional: | |
| Dye | q.s. |

The composition is prepared by combining the above ingredients to achieve the required consistency. The composition is in the form of a "sticky" gel".

If desired, the composition can further comprise an anti-inflammatory agent (e.g. meloxicam 0.1%, 1 mg/ml), and/or a bittering agent.

If desired, lignocaine can be swapped out and tetracaine swapped in at about 1-10%, but preferably about 5% (50 mg/mL).

Example 7—Formulation of a Pain Relieving Composition for Wounds

This Example describes the preparation of another preferred pain relieving composition. The composition is in most respects the same as the composition of Example 2, except that it has tetracaine as both a rapid onset and long duration anaesthetic agent. The composition has the following formulation:

| | |
|---|---|
| Purified water Sorbitol Liquid 70% Non-Crystallising | 100.0 mg/mL |
| Tetracaine HCl | 50.0 mg/mL (5%) |
| Sodium Metabisulfite | 1.5 mg/mL |
| Cetrimide | 5.0 mg/mL |
| Adrenaline Tartrate | 45.0 µg/mL |
| Hydroxy Cellulose | 5.0 mg/mL |
| Purified water | to 1 mL |
| Optional: | |
| Food Dye (e.g. brilliant blue) | Quantity to suit (q.s.) |

The composition is prepared by combining/blending the above ingredients to achieve the required consistency.

If desired, the composition can further comprise an insecticide/insect repellent such as cyromazine or spinosad (at about 1 mg/mL), an NSAID (e.g. meloxicam 0.1% 1 mg/ml), and/or a skin penetrating enhancer.

Example 8—Manufacture of a Sterile Wound Dressing

Figure 1:
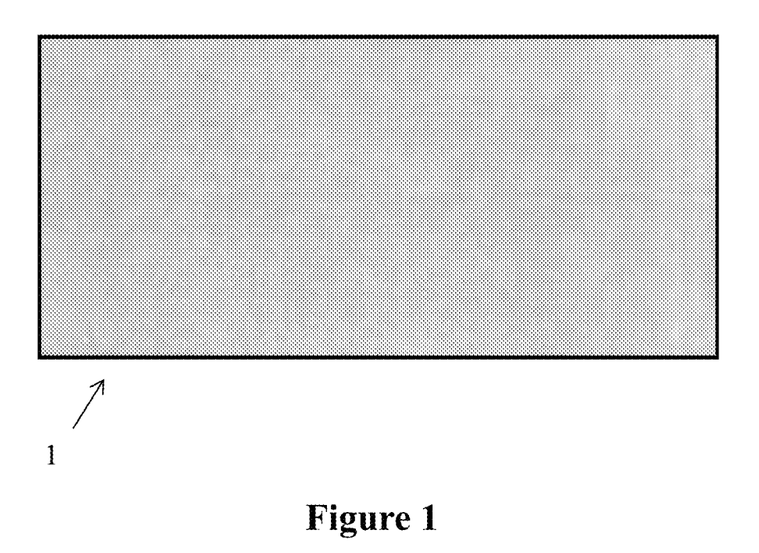
FIG. 1 is picture of a dressing of a sterile wound dressing according to an embodiment of the present invention.
Figure 2:
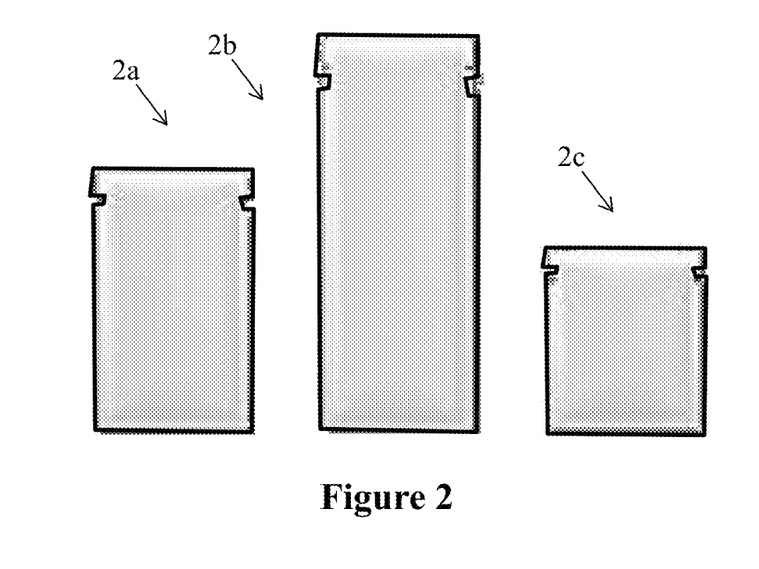
FIG. 2 are pictures of various sized sachets containing the dressing shown in FIG. 1.
Figure 3:
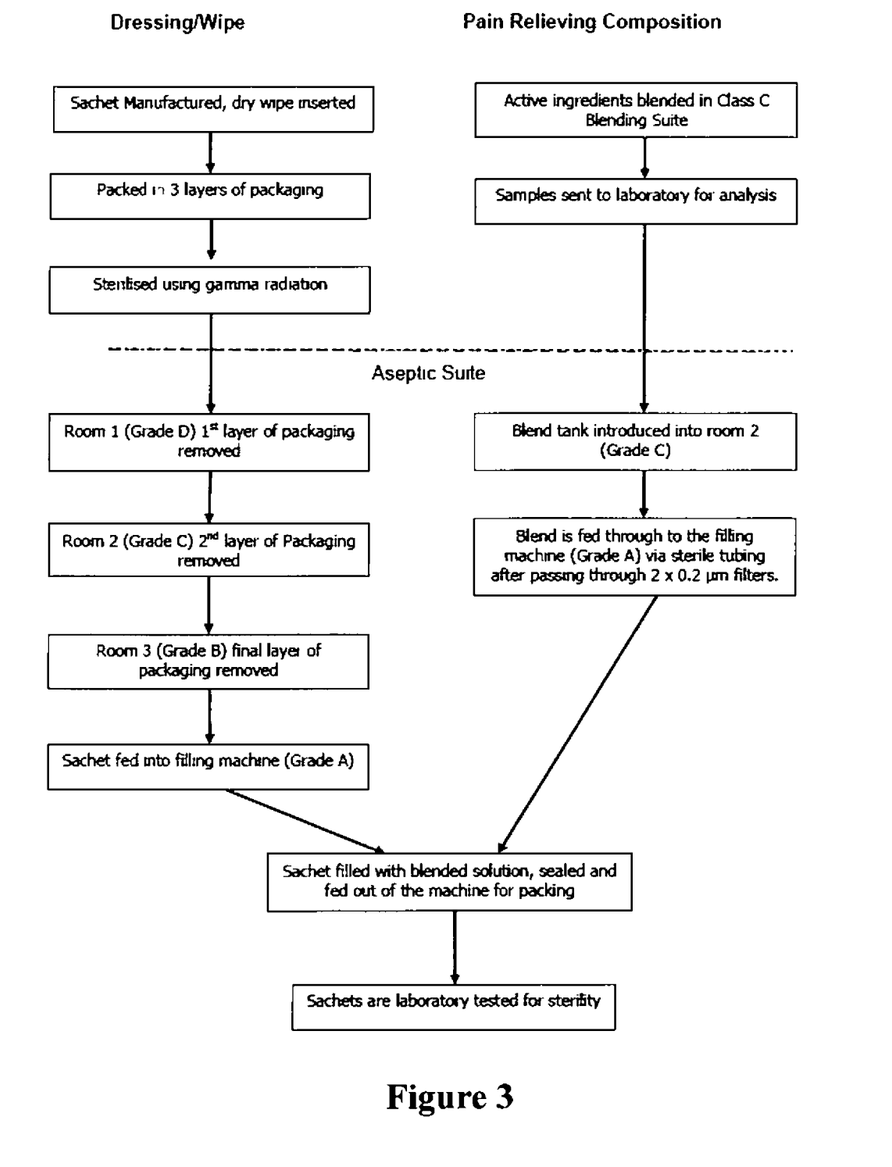
FIG. 3 is a flow chart showing steps in the manufacture of the sterile wound dressing.
Figure 4:
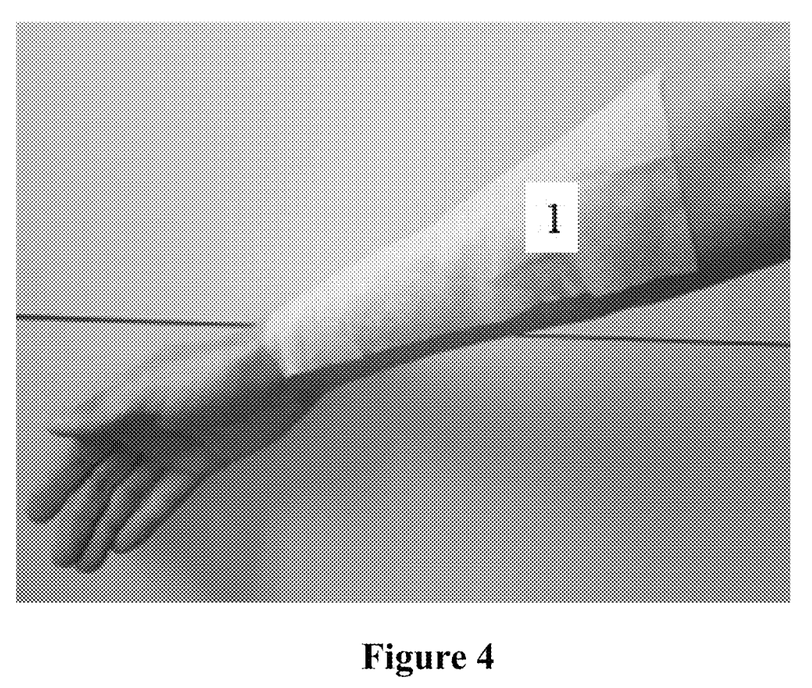
FIG. 4 is a photograph showing application of the dressing to a forearm of a person.

This Example describes the preparation of a sterile wound dressing comprising sterile packaging (sachet) and a dressing saturated with the pain relieving composition of any one of Examples 1 to 7. FIG. 1 shows the dressing 1 saturated with the pain relieving composition. FIG. 2 shows suitable sachets 2a, 2b, 2c containing the dressing. FIG. 3 shows the basic manufacturing steps. FIG. 4 shows use of the saturated dressing 1 on an arm of a person.

All manufacturing steps were completed at ambient temperature.

A sachet was made from a six layer mixture of polyester, polyethylene and aluminium, its weight was approximately 120 gsm. It was chosen for its low linting properties.

A dry 100% polyester dressing/wipe was inserted into the sachet. It was gamma irradiated, packaging layers were removed, and the sachet was then fed into a filling machine. The dry folded dressing/wipe in the open sachet was Gamma irradiated at a minimum of 25 kgy and a maximum of 45 kgy.

The filling machine was an adapted form of a fill and seal machine that was generally used for manufacture of an individual towelette in a sachet.

The pain relieving composition was prepared as described in Examples 1 to 7. The composition ingredients were blended together in a tank and then passed through two 0.2 micron filters, before being fed to the filling machine. Each filter was a 3M sterile life assure Pda filter capsule (0.2 micron).

Trial batches were manufactured in a 50 litre tank. Commercial production will be carried out in an 800 litre tank.

The filling machine filled each sachet with 7 ml of the pain relieving composition. Each sachet was then sealed and fed out of the machine for packing. Each sachet was sealed by heat at a temperature of approximately 140/150° C.

Example 9—Use of the Sterile Wound Dressing of Example 8 on a Wound

This Example describes the use of the sterile wound dressing on a wound of a person's forearm. See FIGS. 1, 2 and 4.

A sterile wound dressing sachet 2a, 2b, 2c was torn open and the dressing 1 removed. The dressing 1 was placed over a wound of forearm of a person, as shown in FIG. 4. The pain relieving composition (stained blue) which supersaturated the dressing 1 was absorbed by the wound and provided pain relief. After a suitable period of time, the dressing 1 was removed. The dressing 1 can also be used as a wipe to debride the wound or otherwise clean the wound or surrounding area.

Advantages of the present invention as exemplified include that the wound dressing can be used to reduce or minimise pain in a large variety of situations in which anaesthetic agents are not currently used by virtue of being too impractical, dangerous, complex, costly, difficult to transport or apply.

Quite frankly, the present inventor did not envisage that a dressing saturated with a pain relieving agent in a sterile sachet could work so well and so have so many potential applications.

Advantages of the present invention as exemplified include:

- it was not envisaged that a saturated dressing in a satchel could work so well.
- it is an anaesthetising dressing.
- it is a vasoconstricting dressing.
- the active/agents are uniformly dispersed throughout the entire dressing.
- it provides a metered dose.
- the sachet is easily transportable and storable.
- the dressing can be used to cover large wounds.
- there is no pain relieving composition run-off
- the pain relieving composition is delivered exactly where required.
- there is no pain relieving composition wastage.
- lots of dressings can be wrapped around large areas, such as burn areas.
- the dressing is supersaturated with pain relieving agent.
- holding the dressing in a sachet with the pain relieving composition causes supersaturation.
- the dressing can provide a homogenous effect across the whole wound.
- the dressing can wrap around body parts.
- the dressing can cover large surface areas.

Throughout this specification, unless in the context of usage an alternative interpretation is required, the term "comprise" (and variants thereof such as "comprising" and "comprised") denotes the inclusion of a stated integer or integers but does not exclude the presence of another integer or other integers.

Any reference to publications cited in this specification is not an admission that the disclosures constitute common general knowledge in Australia or in other countries.

It will be appreciated by one of skill in the art that many changes can be made to the composition and uses exemplified above without departing from the broad ambit and scope of the invention.

Preferred embodiments of the invention are described in the paragraphs below.

1. A wound dressing comprising a dressing saturated with a pain relieving composition:

wherein the dressing is designed to be in direct contact with a wound;
wherein the dressing is supersaturated with the pain relieving composition;
wherein the dressing has an open pore structure or is open weave;
wherein the dressing is anywhere between about 50 and 200 mm wide and about 50 and 300 mm long;
wherein the dressing is made of 100% polyester;
wherein the dressing has one or more of the following properties: it stems wound bleeding; it helps seal the wound; it protects the wound from infection; it eases pain; it promotes healing of the wound; it promotes granulation and epithelialisation of the wound; it prevents further trauma to the wound; it debrides the wound; and, it obscures the wound from view and therefore lessens psychological stress;
wherein the wound dressing is extendible around a limb to cover a large surface area of the limb; and/or
wherein the wound dressing is adapted to be used for an animal husbandry procedure.

2. The wound dressing of paragraph 1, wherein:
the pain relieving composition is in the form of a liquid, ointment, gel, lotion, cream, crème, emulsion, paste, film or suspension;
the pain relieving composition is in the form of a liquid that sets as a sticky viscous gel when exposed to the wound;
the pain relieving composition comprises a hydrophilic or hydroalcoholic gelling agent;
the pain relieving composition comprises about 1 to 20 g per litre of at least one type of gum or cellulosic preparation;
the pain relieving composition comprises a polyhydric alcohol in combination with a cellulosic preparation; or
the pain relieving composition comprises about 5 mg/mL hydroxy cellulose in combination with about 100 mg/mL non-crystallising liquid sorbitol (70%).

3. The wound dressing of paragraph 1 or paragraph 2, wherein the pain relieving composition comprises at least one anaesthetic agent having a rapid onset of action and/or a long duration of action.

4. The wound dressing of paragraph 3, wherein the at least one anaesthetic agent is lignocaine, chloroprocaine, mepivacaine, bupivacaine, articaine, etidocaine, levobupivacaine, tetracaine, prilocaine, benzocaine, ropivacaine, cocaine, oxyprocaine, hexylcaine, dibucaine, piperocaine or procaine, or pharmaceutically acceptable acids, bases and salts thereof.

5. The wound dressing of paragraph 4, wherein the at least one anaesthetic agent having a rapid onset of action is lignocaine, prilocaine, amethocaine/tetracaine or cocaine, and the at least one anaesthetic agent having a long duration of action is bupivacaine, ropivacaine, levo-bupivacaine or amethocaine/tetracaine.

6. The wound dressing of paragraph 4, wherein the at least one anaesthetic agent having both a rapid onset of action and long duration of action, is amethocaine/tetracaine.

7. The wound dressing of any one of paragraphs 1 to 6, wherein the composition comprises:
a vasoconstrictor; or
an antiseptic agent; or
a colouring agent/colourant such that application of the composition to the wound can be easily assessed by eye; or
about 100 mg/mL non-crystallising liquid sorbitol (70%);
about 50.0 mg/mL lignocaine HCl;
about 5.0 mg/mL bupivacaine HCl;
about 1.5 mg/mL sodium metabisulfite;
about 5.0 mg/mL cetrimide;
about 45.0 µg/mL adrenaline tartrate;
about 5.0 mg/mL hydroxy cellulose; and optionally dye; or
about 100 mg/mL non-crystallising liquid sorbitol (70%);
about 40.0 mg/mL lignocaine HCl;
about 1.5 mg/mL sodium metabisulfite;
about 5.0 mg/mL cetrimide;
about 36.0 µg/mL adrenaline tartrate;
about 5.0 mg/mL hydroxy cellulose; and optionally dye; or
about 100.0 mg/mL purified water sorbitol liquid 70% non-crystallising;
about 50.0 mg/mL (5%) tetracaine HCl;
about 1.5 mg/mL sodium metabisulfite;
about 5.0 mg/mL cetrimide;
about 45.0 µg/mL adrenaline tartrate;
about 5.0 mg/mL hydroxy cellulose;
to 1 mL purified water; and optionally
dye; or
lignocaine, bupivacaine, adrenaline, cetrimide, 2-ethyl hydroxycellulose, sodium metabisulfite, liquid sorbitol (70%), buffer, and, optionally, dye; or
amethocaine/tetracaine, adrenaline, cetrimide, 2-ethyl hydroxycellulose, sodium metabisulfite, liquid sorbitol (70%), buffer, and, optionally, dye.

8. The wound dressing of any one of paragraphs 1 to 7, wherein:
(1) the wound dressing is contained within sterile packaging;
(2) the wound dressing is contained within sterile packaging in the form of a tear-open sachet;
(3) the wound dressing is contained within sterile packaging and the sterile packaging contains between about 4-10 ml of the pain relieving composition; or
(4) the dressing is folded into a compact form within the sterile packaging of any one of (1) to (3).

9 A method of providing pain relief due to a wound of a subject, said method comprising the step of applying the wound dressing of any one of paragraphs 1 to 8 to the wound of the subject; or use of the wound dressing of any one of paragraphs 1 to 8 in the preparation of a medicament for providing pain relief due to a wound of a subject.

10. A method of manufacturing a sterile wound dressing according to any one of paragraphs 1 to 8, said method comprising the step of packaging a dressing saturated with a pain relieving composition in a sterile manner so as to produce a sterile wound dressing.

The invention claimed is:
1. A packaged wound dressing comprising a dressing saturated with a pain relieving composition, wherein:
the wound dressing is contained within a sealed sterile packaging;
the wound dressing is folded into a compact form within the sterile packaging;
the sterile packaging is a tear-open sachet;
the wound dressing provides a predetermined therapeutic amount of said pain relieving composition;
the pain relieving composition comprises at least one anaesthetic agent, an antiseptic agent, and a hydrophilic or hydroalcoholic gelling agent;

the pain relieving composition is in the form of a liquid that sets as a sticky viscous gel when exposed to a wound;

the dressing is removable from the wound;

the dressing has an open pore structure or is open weave; and the dressing when unfolded is anywhere between 50 and 200 mm wide and 55 and 300 mm long.

2. The packaged wound dressing of claim 1, wherein the dressing has one or more of the following properties selected from the group consisting of: the dressing is adapted to stem wound bleeding; the dressing is adapted to help seal the wound; the dressing is adapted to protect the wound from infection; the dressing is adapted to ease pain; the dressing is adapted to promote healing of the wound; the dressing is adapted to promote granulation and epithelialisation of the wound; the dressing is adapted to prevent further trauma to the wound; the dressing is adapted to debride the wound; and, the dressing is adapted to obscure the wound from view and therefore lessen psychological stress.

3. The packaged wound dressing of claim 1, wherein the pain relieving composition comprises about 1 to 20 g per litre of at least one type of gum or cellulosic preparation, a polyhydric alcohol in combination with a cellulosic preparation, or about 5 mg/mL hydroxy cellulose in combination with about 100 mg/mL non-crystallising liquid sorbitol (70%).

4. The packaged wound dressing of claim 1, wherein the at least one anaesthetic agent has a rapid onset of action and/or a long duration of action.

5. The packaged wound dressing of claim 4, wherein the at least one anaesthetic agent is selected from the group consisting of lignocaine, chloroprocaine, mepivacaine, bupivacaine, articaine, etidocaine, levobupivacaine, amethocaine/tetracaine, prilocaine, benzocaine, ropivacaine, cocaine, oxyprocaine, hexylcaine, dibucaine, piperocaine and procaine.

6. The packaged wound dressing of claim 1, wherein the composition further comprises a vasoconstrictor.

7. The packaged wound dressing of claim 1, wherein the composition further comprises a colourant such that application of the composition to the wound can be easily assessed by eye.

8. The packaged wound dressing of claim 1, wherein the pain relieving composition comprises lignocaine, bupivacaine, adrenaline, cetrimide, 2-ethyl hydroxycellulose, sodium metabisulfite, liquid sorbitol (70%), buffer, and, optionally, colourant.

9. The packaged wound dressing of claim 1, wherein the pain relieving composition comprises amethocaine/tetracaine, adrenaline, cetrimide, 2-ethyl hydroxycellulose, sodium metabisulfite, liquid sorbitol (70%), buffer, and, optionally, colourant.

10. The packaged wound dressing of claim 1, wherein the pain relieving composition comprises:
   about 100 mg/mL non-crystallising liquid sorbitol (70%);
   about 50.0 mg/mL lignocaine HCl;
   about 5.0 mg/mL bupivacaine HCl;
   about 1.5 mg/mL sodium metabisulfite;
   about 5.0 mg/mL cetrimide;
   about 45.0 µg/mL adrenaline tartrate;
   about 5.0 mg/mL hydroxy cellulose; and
   optionally colourant.

11. The packaged wound dressing of claim 1, wherein the pain relieving composition comprises:
   about 100 mg/mL non-crystallising liquid sorbitol (70%);
   about 40.0 mg/mL lignocaine HCl;
   about 1.5 mg/mL sodium metabisulfite;
   about 5.0 mg/mL cetrimide;
   about 36.0 µg/mL adrenaline tartrate;
   about 5.0 mg/mL hydroxy cellulose; and
   optionally colourant.

12. The packaged wound dressing of claim 1, wherein the pain relieving composition comprises:
   about 100.0 mg/mL sorbitol liquid 70% non-crystallising;
   about 50.0 mg/mL (5%) tetracaine HCl;
   about 1.5 mg/mL sodium metabisulfite;
   about 5.0 mg/mL cetrimide;
   about 45.0 µg/mL adrenaline tartrate;
   about 5.0 mg/mL hydroxy cellulose; and
   optionally colourant.

* * * * *